US008543193B2

(12) United States Patent
Satin et al.

(10) Patent No.: US 8,543,193 B2
(45) Date of Patent: Sep. 24, 2013

(54) METHOD AND APPARATUS FOR RAPID INTERPRETIVE ANALYSIS OF ELECTROCARDIOGRAPHIC WAVEFORMS

(75) Inventors: Scott L. Satin, Washington, DC (US); Robert G. Cochran, New Market, MD (US); Nirmal R. Patel, Croydon, PA (US)

(73) Assignee: Cardiocore Lab., Inc., Bethesda, MD (US)

( * ) Notice: Subject to any disclaimer, the term of this patent is extended or adjusted under 35 U.S.C. 154(b) by 2076 days.

(21) Appl. No.: 11/383,381

(22) Filed: May 15, 2006

(65) Prior Publication Data

US 2006/0264769 A1    Nov. 23, 2006

Related U.S. Application Data

(60) Provisional application No. 60/680,525, filed on May 13, 2005.

(51) Int. Cl.
*A61B 5/0402* (2006.01)

(52) U.S. Cl.
USPC .......................................................... 600/509

(58) Field of Classification Search
USPC ........................................ 600/509, 515, 523
See application file for complete search history.

(56) References Cited

U.S. PATENT DOCUMENTS

| 4,583,553 | A | 4/1986 | Shah et al. |
| 4,989,610 | A | 2/1991 | Patton et al. |
| 5,224,486 | A * | 7/1993 | Lerman et al. ............... 600/509 |
| 5,311,867 | A | 5/1994 | Kynor |
| 5,792,065 | A | 8/1998 | Xue et al. |
| 6,463,320 | B1 | 10/2002 | Xue et al. |
| 6,507,753 | B1 | 1/2003 | Xue et al. |
| 6,564,090 | B2 | 5/2003 | Taha et al. |
| 6,778,852 | B2 | 8/2004 | Galen et al. |
| 2004/0054295 | A1 | 3/2004 | Ramseth |
| 2005/0027201 | A1 * | 2/2005 | Badilini et al. ............... 600/509 |

FOREIGN PATENT DOCUMENTS

| EP | 0 489 209 A1 | 6/1992 |
| JP | 10-85197 A | 4/1998 |
| WO | 88/10093 A1 | 12/1988 |

OTHER PUBLICATIONS

Notice of Oral Hearing dated Oct. 12, 2011 issued by the Government of India Patent Office in counterpart Indian Patent Application No. 2040/MUMNP/2007.
Office Action dated Oct. 31, 2011 issued by the Japanese Patent Office in counterpart Japanese Patent Application No. 2008-511462.

(Continued)

*Primary Examiner* — Eric D. Bertram
(74) *Attorney, Agent, or Firm* — Ropes & Gray LLP

(57) ABSTRACT

A method for analyzing a subject-visit group of ECG waveforms captured digitally on an electrocardiograph machine, on a Holter monitor device or digitized from paper electrocardiograms. A cardiologist selects a subject-visit group from a number of subject-visit groups, and each ECG waveform of the subject-visit group is scanned for artifact. Those ECG waveforms containing artifact are annotated appropriately. A determination is made if measurement calipers are present in each ECG waveform, measurement calipers are added to ECG waveforms lacking measurement calipers, and a preliminary interpretation is assigned to each ECG waveform that lacks a preliminary interpretation. Each ECG waveform is assigned a grouping metric, and the ECG waveforms are segregated according to their grouping metric for display and evaluation.

10 Claims, 10 Drawing Sheets

(56) References Cited

OTHER PUBLICATIONS

Galix ECG Professional Station, GALIX ECG-PS. Computerized Electrocardiography, FDA Section-5, Operational manual, ver. 2.2, Mar. 1, 2003, ¶¶ 2.7-2.9.

Semi-supervised learning of probabilistic models for ECG segmentation, Proceedings of 26th Annual Conference of the IEEE EMBS, San Francisco, USA,. Sep. 1-5, 2004, p. 1, ¶ 1.

* cited by examiner

METHOD AND APPARATUS FOR RAPID INTERPRETIVE ANALYSIS OF ELECTROCARDIOGRAPHIC WAVEFORMS

CROSS-REFERENCES TO RELATED APPLICATIONS

This application claims priority from U.S. Provisional Application No. 60/680,525, filed on May 13, 2005, in the United States Patent and Trademark Office, the disclosure of which is incorporated herein in its entirety by reference.

BACKGROUND OF ILLUSTRATIVE EMBODIMENTS OF THE INVENTION

The heart is a pump comprised of muscle tissue that responds to electrical stimulation. A heartbeat is a precisely controlled event that relies on synchronization between the atrial and ventricular chambers to maximize pumping efficiency. The sinoatrial node, which is located in the right atrium of the heart, generates the electrical stimulus. In a healthy person, the sinoatrial node normally generates electrical stimulus signals at a 60-100 Hz rate, and the waves of myocardial excitation and contraction spread throughout the heart in well-defined manner. The electrical stimulus signals cause contractions in the heart's chambers, thereby pumping blood through the chambers. The left and right atria of the heart contract first and for a brief time, and then the left and right ventricles contract for a brief time. Normal heart rhythm is referred to as "sinus" rhythm, because it originates in the sinoatrial node (also referred to as the sinus node). The electrical stimulus signal output by the sinoatrial node is first sent to the left and right atria, then through the atrioventricular node and into the left and right ventricles.

An electrocardiogram ("ECG") measures the heart's electrical activity. Electrodes are placed at specific locations on the body to capture a tracing of the heart's electrical activity. The electrical activity resulting from heart depolarization and heart repolarization is recorded by each lead. The ECG is a summation of the information recorded from each lead. The captured ECG reflects the direction of electrical current flow, and the magnitude of the muscle that is depolarized. Therefore, when the atria depolarize (and contract) the ECG tracing is smaller as compared to when the ventricles contract, since the atria are much smaller than the ventricles. Ventricle repolarization is in the same direction (positive) as ventricle depolarization. Although an ECG is positive during membrane depolarization and negative during repolarization, the direction with respect to ventricles is the same since ventricles depolarize from the inside to the outside (endocardium to epicardium), while repolarization occurs in the opposite direction.

Referring to FIG. 1, an ECG tracing is illustrated. The cardiac cycle begins with a P-wave, wherein the spontaneously firing cells in the sinoatrial node reach a threshold and generate action potentials. A wave of depolarization spreads to the left and downward though left and right atria, which is labeled in FIG. 1 as the "P wave." The atria that were hyperpolarized suddenly become depolarized, and the ECG records a positive deflection. When the left and right atria become depolarized, the ECG returns to zero. The electrical current passes through the atrioventricular node, causing a delay of about one-tenth of a second. Due to the small mass of the atrioventricular node, the ECG tracing does not record any electrical activity. When the atrioventricular node is depolarized, it triggers depolarization of the Purkinje fibers. The Purkinje fibers spread the electrical current throughout the left and right ventricles, thereby causing depolarization across each ventricle simultaneously. Since the tissue mass of the Purkinje fibers is small, the ECG tracing does not record any electrical activity. The passing of the electrical current through the atrioventricular node and the Purkinje fibers is labeled in FIG. 1 as the "PR segment."

The depolarization of the left and right ventricles is referred to as the "QRS complex," and FIG. 1 is labeled as such. The QRS complex is quite large since the left and right ventricle tissue is large in comparison to the sinoatrial node. The three peaks are indicative of the manner in which the electrical current spreads through the left and right ventricles (i.e., from inside to outside) and indicative of the fact that the tissue mass of the left ventricle is greater than the tissue mass of the right ventricle. The complete depolarization of the left and right ventricles indicates that the QRS complex has terminated.

Referring to FIG. 2, the points of the QRS complex are labeled. As noted above, the QRS complex is indicative of the depolarization of the left and right ventricles. The ventricular depolarization begins at a left side of the intraventricular septum, and the peak of this depolarization is shown by the "Q" peak of the QRS complex. The ventricular depolarization spreads from the endocardial surface of the left ventricle to the epicardial surface of the left ventricle, and is shown by the "R" peak of the QRS complex. The spread of the ventricular depolarization to the right ventricle is shown by the "S" peak of the QRS complex.

The segment labeled "T wave" in FIG. 1 indicates repolarization of the left and right ventricles. Although the left and right ventricles are repolarizing, the T wave is positive, since the heart repolarizes from outside to inside, which is the opposite direction of depolarization (inside to outside). The completion of the T wave signals marks the end of the cardiac cycle.

Referring to FIG. 3, the captured tracing of electrical activity is printed out on a paper tape or is presented on a display. Anomalies in an ECG waveform are indicative of various heart-related conditions, such as ischemia, myocardial infarction, conduction disorder, electrolyte disturbance, pericarditis, valve disease or enlarged heart. Certain arrhythmias might occur only on an intermittent basis, or only if certain psychological or physical factors (i.e., stress, fatigue, etc.) are present. Since a typical ECG tracing is only a few minutes in length, arrhythmias of this type are difficult to capture. A more lengthy ECG tracing, referred to as a Holter monitor, is used to capture any arrhythmias or other abnormal activity. The Holter monitor may record a heart's activity over a period of several days.

Referring to FIG. 1, one of the segments that is measured is the referred to as the QT interval, and the QT interval indicates the duration of the electrical activity that controls contraction of the cells of the heart muscle. The QT interval represents the duration of ventricular depolarization and subsequent repolarization, beginning at the initiation of the Q wave of the QRS complex and ending where the T wave returns to the isoelectric baseline. QT interval prolongation creates an electrophysiological environment that favors the development of cardiac arrhythmias, most commonly torsade de pointes, but possibly other ventricular arrhythmias as well. Long QT syndrome identifies a condition wherein there exists an abnormally long QT interval on the ECG tracing. The term "congenital long QT" refers to a long QT interval that is inherited. The inherited form occurs due to irregularities in particular heart cell proteins, and, of course, these protein irregularities are caused by abnormalities in the genes that produce those proteins. The term "acquired long QT" refers to a long QT interval that is brought about by drugs or anomalous levels of the salts within blood (e.g., potassium and magnesium).

Although a person might have an unremarkable QT interval under normal conditions, that person might develop a prolonged QT or suffer torsades de pointes ("TdP") when taking certain medications. As shown in FIG. 4, TdP refers to the characteristic appearance of the electrocardiogram indicative of a rhythm abnormality, and typically occurs in the setting of a prolonged QT interval on the electrocardiogram. TdP is a polymorphic ventricular tachyarrhythmia that manifests on the ECG tracing as continuous twisting of the vector of the QRS complex around the isoelectric baseline. A feature of TdP is pronounced prolongation of the QT interval in the sinus beats preceding the arrhythmia. TdP can degenerate into life-threatening cardiac rhythms that can result in blackouts or sudden death. Measurement of the QT interval on the ECG tracing is still the main method of determining whether a person has long QT interval syndrome, whether inherited or acquired.

Non-antiarrhythmic drugs can have an undesirable side effect of causing delayed cardiac repolarization. Due to its relationship to heart rate, the QT interval is normalized into a heart rate independent "corrected" value known as the $QT_c$ interval, which represents the QT interval at a standardized heart rate (essentially the QT interval at a heart rate of 60 bpm). Several drugs that have caused TdP clearly increase both the absolute QT interval and the $QT_c$ interval.

SUMMARY OF ILLUSTRATIVE EMBODIMENTS OF THE INVENTION

Illustrative, non-limiting embodiments of the present invention overcome various disadvantages. In addition, the present invention is not required to overcome these disadvantages, and an illustrative, non-limiting embodiment of the present invention may not overcome any disadvantages.

According to one embodiment, a method for analyzing a subject-visit group of ECG waveforms is provided. In one implementation, the method selects a subject-visit group from a plurality of subject-visit groups, scans each ECG waveform of the subject-visit group for artifact, and annotates ECG waveforms containing artifact. Also, the method determines if measurement calipers are present in each ECG waveform and adds measurement calipers to ECG waveforms lacking measurement calipers. The method also comprises assigning a preliminary interpretation to each ECG waveform that lacks a preliminary interpretation. Furthermore, the method assigns a grouping metric to each ECG waveform and segregates ECG waveforms according to their grouping metric for display and evaluation.

According to another embodiment, an apparatus and software routine that perform the method are provided.

Additional aspects of the illustrative, non-limiting embodiments of the invention will be set forth, in part, in the description that follows. Also, one of ordinary skill in the art may learn other aspects by performing routine experimentation after reviewing the application.

BRIEF DESCRIPTION OF THE DRAWINGS

Features and advantages of illustrative, non-limiting embodiments of the invention will become more apparent by describing some of the embodiments in detail. The drawings, which are incorporated in and constitute a part of this specification, illustrate some of the exemplary embodiments. In the drawings.

Figure 1:
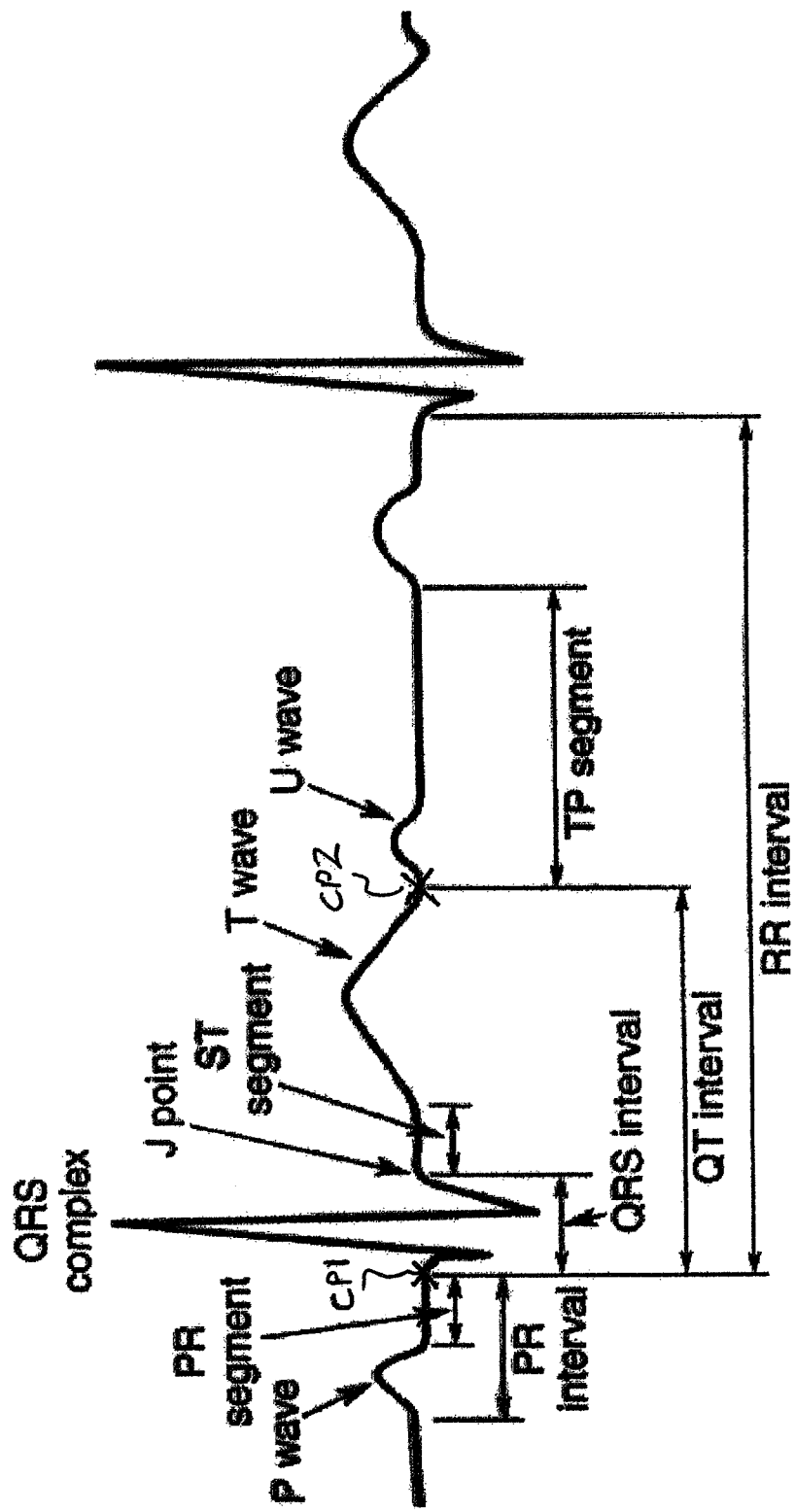
FIG. 1 is an illustration of an ECG tracing that identifies the various segments of an electrical profile of a normal heartbeat.

DETAILED DESCRIPTION OF THE ILLUSTRATIVE, NON-LIMITING EMBODIMENTS OF THE INVENTION

Illustrative, non-limiting embodiments of the present invention will now be described more fully with reference to the accompanying drawings. A general example of a computer (not shown) that can be used in accordance with one embodiment will be described below.

The computer comprises one or more processors or processing units, a system memory, and a bus that couples the various system components. The bus can be one or more of any of several types of bus structures, comprising a memory bus or memory controller, a peripheral bus, an accelerated graphics port and a processor, or local bus using any of a variety of bus architectures. The system memory comprises read only memory ("ROM") and random access memory ("RAM"). A basic input/output system ("BIOS") may contain routines that help transfer information between elements within the computer, such as during boot up. The BIOS may be stored in the ROM or in a separate memory.

The computer further comprises a hard drive for reading from and writing to one or more hard disks (not shown). Some computers comprise a magnetic disk drive for reading from and writing to a removable magnetic disk and/or comprise an optical disk drive for reading from or writing to a removable optical disk, such as a CD ROM or other optical media. The hard drive, the magnetic disk drive, and the optical disk drive are connected to the bus by an appropriate interface. The drives and their associated computer-readable media provide nonvolatile storage of computer-readable instructions, data structures, program modules, and other data for the computer. Although the exemplary environment described herein employs a hard disk, a removable magnetic disk, and a removable optical disk, it should be appreciated by those skilled in the art that other types of computer-readable media, such as magnetic cassettes, flash memory cards, digital video disks, RAMs, ROM, carrier waves, transmissions, etc., may also be used.

A number of program modules may be stored on the hard disk, magnetic disk, optical disk, ROM or RAM, and these modules typically comprise an operating system, at least one or more application programs, other program modules, and program data. In some computers, a user might enter commands and information into the computer through input devices such as a keyboard and a pointing device. Other input devices (not shown) may comprise a microphone, a joystick, a game pad, a satellite dish and/or a scanner. In some instances, however, a computer might not have these types of input devices. These and other input devices are connected to the processing unit through an interface coupled to the bus. In some computers, a monitor or other type of display device may also be connected to the bus via an interface, such as a video adapter. Some computers, however, do not have these types of display devices. In addition to monitors, the computers may have other peripheral output devices (not shown) such as speakers and printers.

A computer can, but need not, operate in a networked environment using logical connections to one or more remote computers. A remote computer may be another personal computer, a server, a router, a network PC, a peer device, or other common network node, and typically comprises many or all of the elements described above relative to the computer. The logical connections to the computer may comprise a local area network ("LAN") and a wide area network ("WAN"). Such networking environments are commonplace in offices, enterprise-wide computer networks, intranets, and the Internet.

When used in a LAN networking environment, the computer is connected to the local network through a network interface or adapter. When used in a WAN networking environment, the computer typically comprises a modem or other means for establishing communications over the wide area network, such as the Internet. The modem, which may be internal or external, is connected to the bus via a serial port interface. In a networked environment, program modules for the computer, or portions thereof, may be stored in a memory storage device of a remote computer. It will be appreciated that the network connections shown are exemplary and that other means of establishing a communications link between the computers may be used.

Generally, the data processors of the computer are programmed with instructions stored at different times in the various computer-readable storage media of the computer. Programs and operating systems are typically distributed, for example, on floppy disks or CD-ROMs. From there, they are installed or loaded into the secondary memory of the computer. At execution, they are loaded at least partially into the computer's primary electronic memory. Illustrative, non-limiting embodiments of the invention may comprise these and other various types of computer-readable storage media, which contain instructions or programs for implementing the operations described below in conjunction with a microprocessor or other data processor. Some embodiments may also comprise the computer itself when it is programmed according to the methods and techniques described below.

One exemplary embodiment of the present invention comprises a method and apparatus for assisting cardiologists in evaluating ECG waveforms. The embodiment may contain a computer that simulates a relatively inexperienced cardiologist who is assisting an expert cardiologist in interpreting captured ECG tracings. These ECG tracings or waveforms may be captured digitally via an electrocardiograph machine or via a Holter monitor device, or they may be digitized from paper electrocardiograms.

In one implementation, the computer identifies artifacts in the ECG tracings and tentatively interprets the ECG tracings. Also, the computer may compare several ECG waveforms based on information known about the waveforms and may group the waveforms accordingly.

For instance, if a cardiologist has marked one waveform as a normal waveform and has marked another waveform as an abnormal waveform, the computer may determine that both waveforms cannot be members of the same group, even if they have some characteristics in common. In addition, if a cardiologist changes the computer's interpretation of the waveform, the computer may analyze the changes and regroup the remaining waveforms based on the changes.

Also, ECG tracings are stored in a variety of different file formats, such as FDA XML, Mortara XML (as exported from E-Scribe), and GE® MUSE®. As such, the computer may include conversion libraries that facilitate the conversion of the ECG tracings, which are stored in one of these formats, into a format that the computer uses. Thus, the conversion libraries allow the computer to process ECG tracings having a uniform format, without having to worry about the specific format, sample rate, length of recording or other details of the data for the original ECG tracings. Accordingly, the embodiment operates independently of the data file size, format, sample rate, bit depth and scale factor.

Also, a Holter recording file typically will contain 24 or 48 hours of 12-lead data at 1 k samples per second. In one embodiment of the present invention, the computer can process a Holter recording of at least 48 hours×12 leads×1 k samples per second. However, the present invention clearly is not limited to such an embodiment, and the computer may be able to handle longer recordings or recordings taken at higher and/or lower sampling rates.

Figure 5:
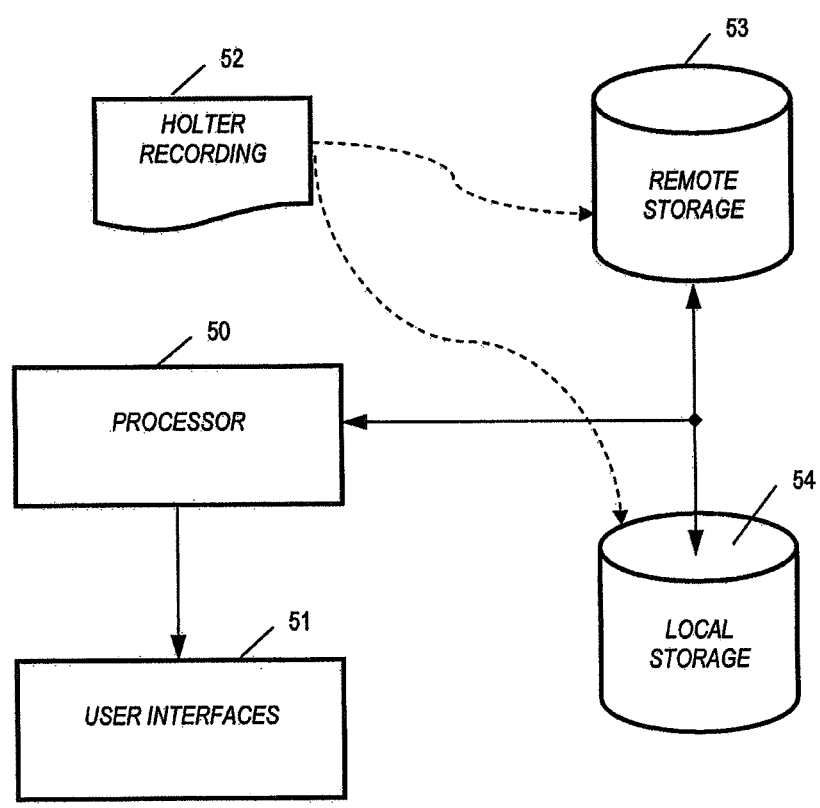
FIG. 5 is an illustration of a non-limiting example of a computer system for extracting segments from a Holter recording for analysis.

FIG. 5 shows an example of a computer that may be used in an illustrative, non-limiting embodiment of the present invention. The computer comprises a processor 50, user interfaces 51, and local storage 54. As described above, the processor 50 may comprise one or more processors, and the user interfaces 51 may comprise monitors, keyboards, mice, touch-screens, etc. The processor 50 is connected to the local storage 54 via a bus (or busses), and the local storage 54 may comprise various types of disk memories, electronic memories (i.e., RAM, ROM, etc.), or various combinations thereof. The processor 50 may also access a remote storage 53, which may comprise various types of data storage machines and/or server machines.

The remote storage 53 or the local storage 54 stores a Holter recording file 52. Also, while the storage 53 or 54 stores the Holter recording file 52 in the present example, the remote storage 53 or local storage 54 may additionally or alternatively store digital ECG waveforms captured via other means. For example, the storage 53 or 54 may store a waveform captured via an electrocardiograph machine or digitized from paper electrocardiograms. In any event, the processor 50 accesses the Holter recording file 52 from the storage 53 or 54.

Although there is no set time limit on the length of an ECG tracing within the Holter recording file 52, the typical length of an ECG tracing is about ten seconds. In the present embodiment, the time limit for the tracing is configurable, and a default time limit is ten seconds. Also, in one implementation, the computer truncates ECG tracings that are longer than the configured time limit.

The computer may also process three aspects of data. The first aspect is a Subject-Visit Group ("SVG"). The SVG is a set of all ECG tracings taken for a given test subject, and these tracings may be taken during a single visit to the research facility or during a single day's recording. The second aspect is a single ECG tracing, which is typically ten seconds in length, though other time lengths are possible. The ECG tracing may be extracted from a long or continuous recording or it may be captured separately. Additional information regarding the extraction of ECG tracings from a continuous recording is disclosed in the co-pending utility application which is entitled "Method and Apparatus for Sequenced Extraction from Electrocardiographic Waveforms," which was invented by S. Satin, R. Cochran, and N. Patel, which was filed on May 15, 2006, and which is based on U.S. Provisional Appln. No. 60/680,524. The disclosure of these utility and provisional applications are incorporated herein by reference for all purposes. The third aspect is an ECG waveform, which is a short portion of an ECG tracing and represents a single heartbeat. The length of the ECG waveform will vary with the heart rate.

In the embodiment, the computer processes and displays one or more ECG tracings within a particular SVG, one SVG at a time, and the cardiologist can evaluate and interpret the display tracing or tracings. After the cardiologist finishes evaluating all of the tracings within an SVG, the computer selects the next SVG for the cardiologist examine. In one implementation, the computer selects the next SVG based on which SVG has been stored for the longest period of time without being interpreted. Alternatively, the computer could select the next SVG based on the results of a preliminary interpretation or based on the results of a preliminary (but non-interpretive) screening. The preliminary interpretation or screening may be done by a human technician or by an automatic computerized process. Of course, the cardiologist is free to select a particular SVG, as opposed to being limited to viewing and interpreting the tracings in SVGs, which have been prioritized in any particular order.

After the cardiologist or computer selects an SVG for interpretation, the cardiologist or computer can examine each ECG waveform to determine if the waveforms contain "artifact." Artifact corresponds to ECG waveform data that is corrupted or has been affected by excessive noise. If an ECG waveform contains artifact, it is marked accordingly.

Also, the computer may evaluate each ECG waveform in the SVG to determine the location of a set of caliper positions. A caliper position marks a point on the ECG waveform, and the distance between a set of two caliper positions on the waveform corresponds to the distance between the corresponding two points on the waveform. In one example, the caliper positions are included as part of the digital data relating to the ECG waveform and can be generated by an ECG recorder, a human technician, a separate a computer process, etc. Also, FIG. 1 shows an illustrative example of two caliper positions CP1 and CP2 that are used to measure the length of the QT interval. As is evident from the figure, the distance between the positions CP1 and CP2 corresponds to the length of the interval.

Also, if the data corresponding to a ECG waveform lacks caliper positions, the computer can analyze the ECG waveform and assign caliper positions for measuring the appropriate portion or portions of the waveform. An example of an algorithm that can analyze a waveform and measure aspects of the waveform is disclosed in U.S. Pat. No. 6,580,817, which is entitled "Apparatus and Method for Reading and Analyzing ECG Images," which was invented by F. Badilini, and which was filed on May 17, 2001. The disclosure of the '817 patent is incorporated herein by reference for all purposes.

Alternatively, the cardiologist can review the ECG waveforms and assign measurement caliper positions thereto via an appropriate software application. For example, when the ECG waveform is displayed, the cardiologist can maneuver a mouse or other input device to assign caliper positions to various positions of the waveform.

The computer may also perform a preliminary interpretation of each ECG waveform, where none exists, to initially and preliminarily associate the waveform with a particular type of waveform. Then, the computer may include or embed data corresponding to the preliminary interpretation in the digital data for the ECG waveform data. Alternatively, a human technician may conduct a preliminary interpretation manually and input the results to the computer. In one implementation, the preliminary interpretation operation evaluates certain characteristics of the ECG waveform and associates it with a particular type of waveform. For example, during a preliminary interpretation, the computer may evaluate various characteristics of the ECG waveform to preliminarily determine if the waveform is corresponds to a normal waveform or an abnormal waveform. Further interpretation may deem that one abnormal waveform represents atrial fibrillation, and another abnormal waveform represents left ventricular hypertrophy.

If the computer performs a preliminary interpretation operation on an ECG waveforms, it may receive feedback from the cardiologist and adjust the manner in which it interprets waveforms based on the feedback. For example, after the computer performs its preliminary interpretation on an ECG waveform, the cardiologist may adjust or correct the interpretation and input these corrections to the computer. Then, the computer may adjust various thresholds, evaluation parameters, etc. of the preliminary interpretation process based on the input corrections.

Typically, conventional interpretation algorithms rely on training from expert cardiologists. In one particular embodiment of the present invention, the cardiologist essentially corrects or confirms the work of the automated preliminary interpretation process that the computer performs, either by changing the computer's interpretation or by accepting a correct interpretation. In either case, the feedback is used to improve the performance of the preliminary interpretation algorithm, on either a batch basis or a real-time (interactive) basis. As a result of this feedback process, the computer's preliminary interpretation of ECG waveforms is improved and the cardiologist's workload is reduced.

After each ECG waveform is examined, a grouping metric is assigned to the waveform. The grouping metric is a set of one or more numeric or non-numeric (i.e., text) values that reflect certain key aspects of each ECG waveform. Accordingly, the computer can evaluate the grouping metrics of two ECG waveforms to determine how similar the ECG waveforms are, in the sense of cardiologic interpretation. In other words, if two ECG waveforms have very similar grouping metrics, then the ECG waveforms are very similar from the cardiologist's point of view.

As one example, a normal ECG waveform has predetermined shape and characteristics. Also, an ECG waveform that represents a certain abnormality likewise has a predetermined shape and characteristics. For example, an abnormal waveform that indicates that a patient has an atrial fibrillation has a first predetermined shape and characteristics. Also, an abnormal waveform that indicates that a patient has a left ventricular hypertrophy has a second predetermined shape and characteristics. Likewise, abnormal waveforms respectively representing a right bundle branch block or sinus bradycardia have other predetermined shapes and characteristics.

Thus, the computer may generate the grouping metrics by comparing the data of an ECG waveform with the data of predetermined normal and abnormal waveforms. For example, the computer can compare corresponding points of the ECG waveform and the predetermined normal waveform and determine the degree to which the ECG waveform varies or deviates from the predetermined normal waveform at these points. In one implementation, computer measures the deviation of the corresponding points by determining how many pixels separate a point of the ECG waveforms from a corresponding point of the predetermined normal waveform. This deviation, in terms of pixels, may be used as one factor for creating the grouping metric. Similarly, the computer may compare the ECG waveform with each of the predetermined abnormal waveforms to determine how the ECG waveform varies from each of the abnormal waveforms and may use these variations as additional factors for creating the grouping metric.

Figure 2:
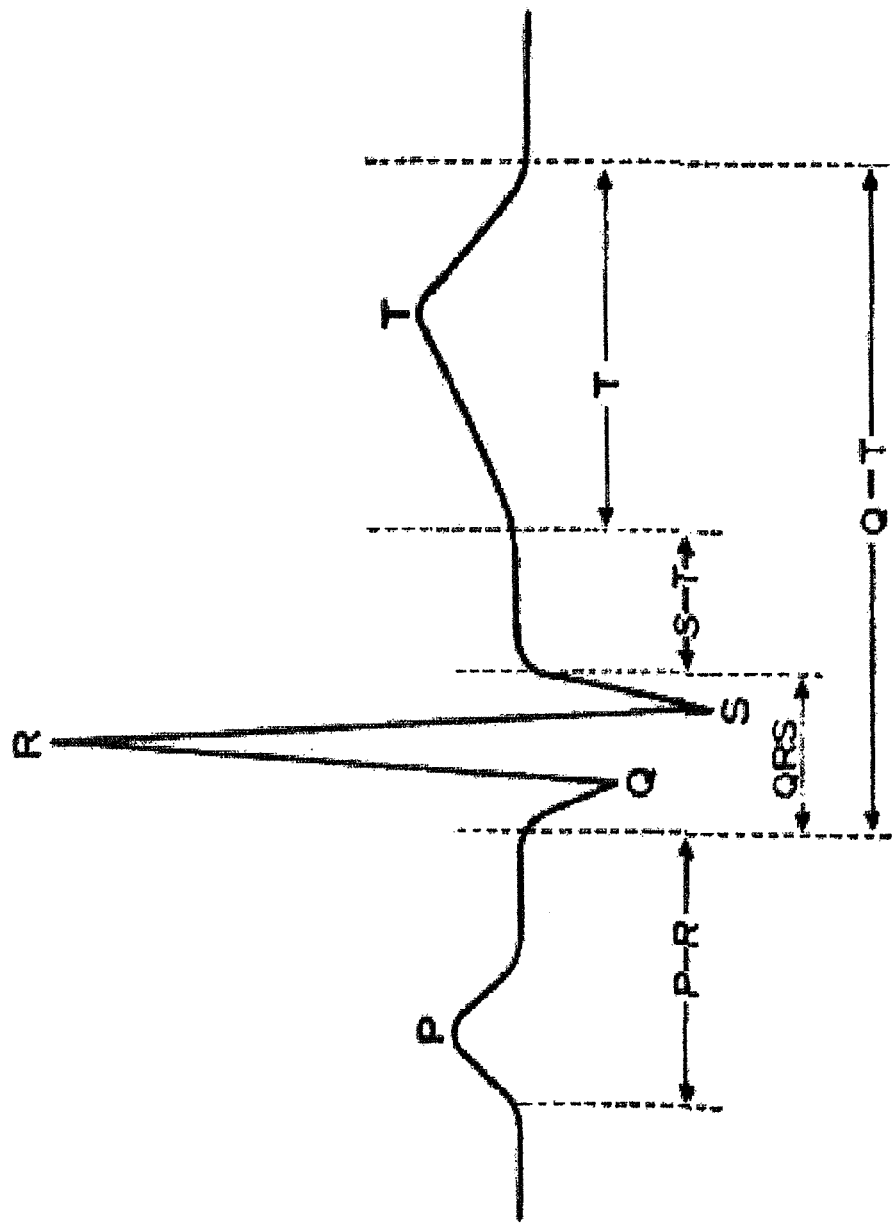
FIG. 2 is an illustration of an ECG tracing that also identifies the various segments of an electrical profile of a normal heartbeat.
Figure 3:
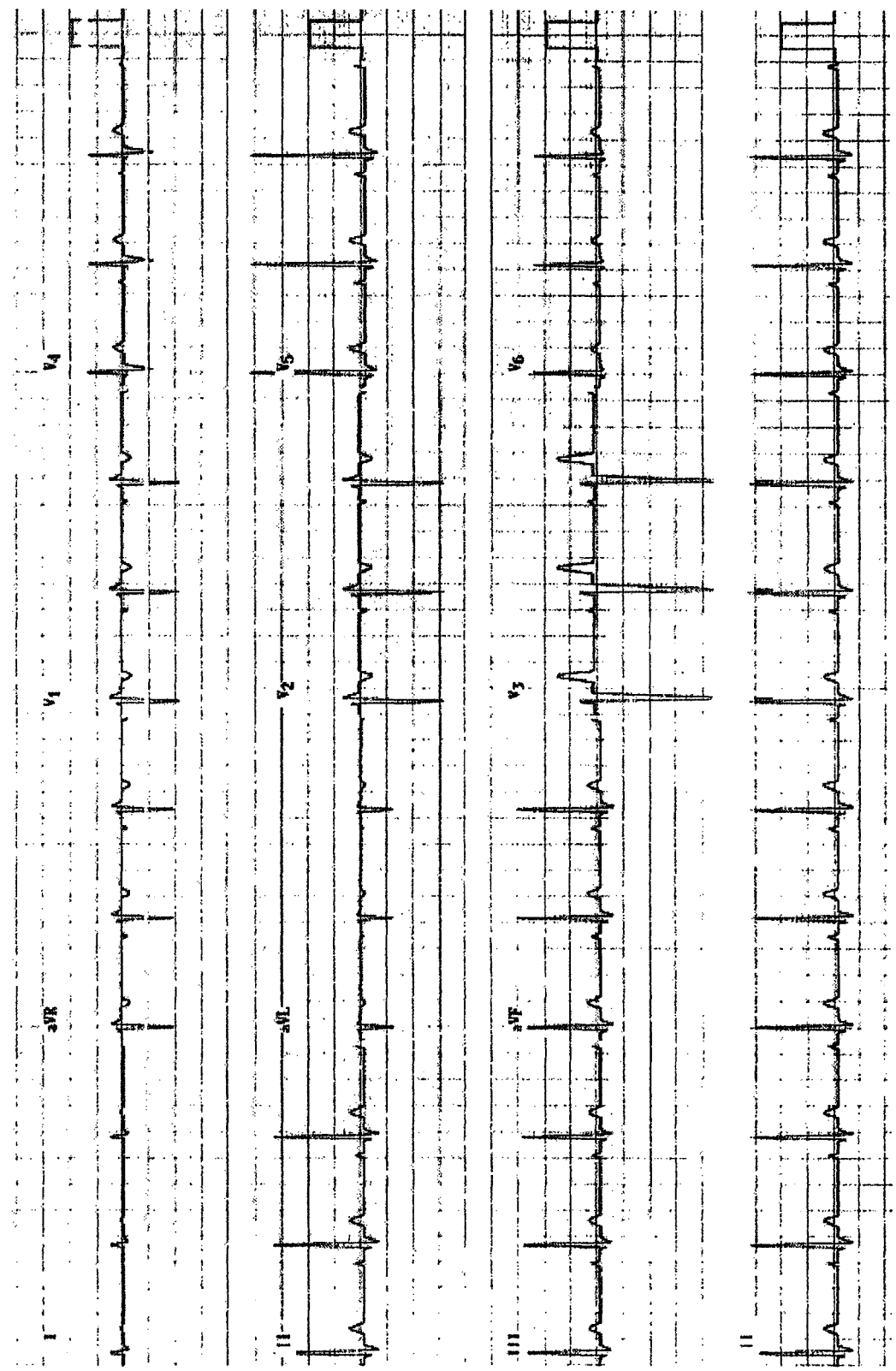
FIG. 3 is an illustration of the output from a 12-lead ECG or Holter monitoring device.
Figure 4:
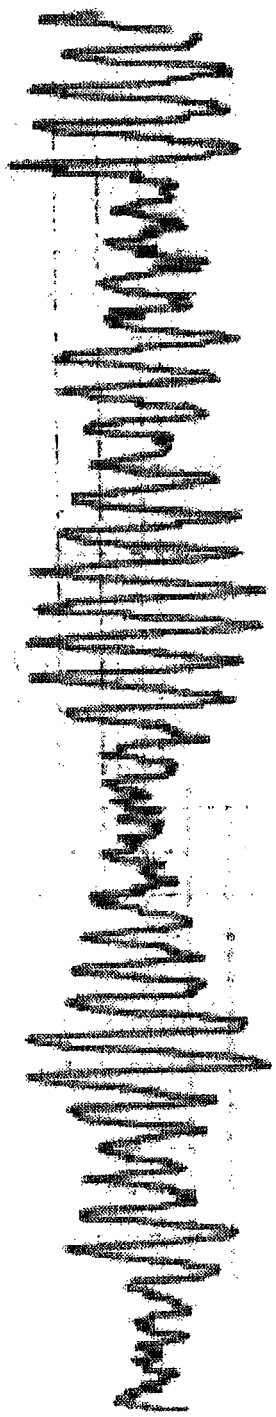
FIG. 4 is an illustration of an ECG tracing showing Torsades de Pointes (TdP)

The computer may also determine whether or not any of the ECG waveforms in the SVG have a preliminary interpretation that is so reliable that it can be accepted without the cardiologist's approval. The computer may evaluate one or more aspects of the preliminary interpretation to determine the reliability of the interpretation. For example, the computer may determine (1) if the waveform has any artifact, (2) if the percentage of artifact in the waveform is less than a predetermined threshold, (3) if the magnitude or degree of an artifact within the waveform exceeds a predetermined threshold, (4) if the slope of the T-wave (FIGS. 1 and 2) is within a predetermined range, etc. If the ECG waveform has a very reliable preliminary interpretation, the computer may exclude the waveform from further analysis to reduce the cardiologist's workload.

Next, the grouping metrics, as well as other available information, of the ECG waveforms in the SVG are examined, and the ECG waveforms are grouped according to how similar they are, from a cardiologic point of view. For example, in one embodiment, the computer may evaluate the amount that the ECG waveform deviates from each of the predetermined normal or abnormal waveforms. If the ECG waveform deviates from one of the predetermined waveforms (e.g., the predetermined abnormal waveform representing atrial fibrillation) by less than a predetermined amount (e.g., less than a predetermined number of pixels), the computer may place the ECG waveform in the "atrial fibrillation waveform" group.

During the grouping analysis, the presence of any artifact, as detected previously or as indicated by the cardiologist, is taken into account. In addition, the presence of any existing preliminary interpretation, cardiologist-provided interpretation, or automatically-accepted interpretation is taken into account as well. If verified measurement caliper positions are available at this point, computer may evaluate these measurements in the grouping analysis, along with the other grouping metrics.

In one example, the computer does not combine an ECG waveform with artifacts and an artifact-free ECG waveform into the same group. Furthermore, in one implementation, each ECG waveform having an artifact is assigned to its own single-member group.

Also, in one embodiment, ECG waveforms with a final, accepted interpretation will not be included in any group at all, regardless of whether the final, accepted interpretation came from a cardiologist or an automatic computer process. On the other hand, all ECG waveforms that lack a confirmed interpretation are placed into one or more groups, according to their similarity, and those groups contain only waveforms that are substantially similar to each other.

The computer may also employ a neural network called a self-organizing map ("SOM") that provides information about the relationships between the groups of ECG waveforms. Thus, in addition to grouping similar ECG waveforms together, a SOM also provides some indication about the relationship between groups of waveforms. Specifically, the SOM arranges the groups in a geometric and/or spatial way such that it places groups, which tend to be similar to each other, adjacent or close to each other.

Also, in an illustrative, non-limiting embodiment, the cardiologist has the ability to control the coarseness or fineness of the grouping of ECG waveforms. For example, when ECG waveforms are grouped, it is possible to group them too tightly (e.g., ECG waveforms that should be in different groups are lumped together) or too loosely (e.g., ECG waveforms that should be combined are grouped apart). Either situation creates more work for the cardiologist because the cardiologist has to study the grouped waveforms and revise the groups. By tightening or loosening the grouping, the cardiologist can optimize the manner in which the computer groups the waveforms.

As one example of tightening or loosening the grouping, the cardiologist can adjust the predetermined maximum amount (e.g., the maximum number of pixels) that an ECG waveform can deviate from a predetermined waveform (e.g., the predetermined atrial fibrillation waveform) and still be grouped in the predetermined waveform group (e.g., the "atrial fibrillation waveform" group). For example, assume that the computer incorrectly includes certain waveforms in the "atrial fibrillation waveform" group. In such case, the cardiologist can instruct the computer to be more selective in deciding which waveform belongs in the "atrial fibrillation waveform" group by decreasing the predetermined maximum amount (e.g., number of pixels) from which a waveform can deviate from the predetermined waveform and still be placed in the group.

Also, the computer may have a single screen to display all of the ECG waveform groups that are associated with a particular SVG. As one example, the screen could have a number of boxes, and each box could show all the ECG waveforms that are assigned to a single group. Also, the computer may overlay the ECG waveforms, and the doctor can select the Holter lead by using a mouse or other device to move a cursor to the lead and select it. If there are too many boxes to fit on the screen at one time, a scrolling display may be created, and the computer may prioritize the groups based on the number of waveforms that they contain. Then, the computer could display the boxes corresponding to the most populous groups at the top of the scrolling display.

By displaying the groups of ECG waveforms in the above manner, the cardiologist can see, at a glance, how the ECG waveforms have been grouped. If the cardiologist believes that the ECG waveforms are grouped too tightly (into too few boxes), the cardiologist can input commands to the computer to regroup the ECG waveforms into a larger number of groups as described above. Likewise, if the ECG waveforms have been split up unnecessarily, the cardiologist can input commands to regroup the ECG waveforms into a smaller number of groups.

Also, the computer may automatically display the groups in a certain order. For example, the computer may display the groups in order of their size, whereby the largest groups, which presumably contain the most common waveforms, are presented first. In another implementation, the computer displays the smallest groups first, as a way of highlighting the least common waveforms seen during the Holter recording. In another instance, the computer uses the pre-existing interpretive statements, in combination with a grading system, to order the groups. For instance, some interpretations that are deemed noteworthy might be displayed ahead of other, less remarkable interpretations. As yet another example, the computer may enable the cardiologist to use the screen for the adjustment of the grouping tightness/looseness and allow the cardiologist view all the ECG waveform groups and select a group for display. Alternatively, the cardiologist may be able to input a command to select which group he or she would like the computer to display.

Once a group of an ECG waveforms is selected for display, the computer decomposes the waveform into one or more batches. For example, the display may not be able to display the entire group of ECG waveforms at once because there may be a limit (based upon the computer hardware and/or software) on how many ECG waveforms can be simultaneously displayed. If not all the ECG waveforms can be displayed, the group of waveforms is divided into batches such that the number of waveforms in each batch is less than or equal to the maximum number of waveforms that the computer can display at once. Also, the batch may contain an entire group of ECG waveforms, if the entire group of waveforms does not exceed the limitations of the computer display.

Then, one of the batches of waveforms of the current group is selected to be presented to the cardiologist, and this batch is called the current display batch. As such, the cardiologist can quickly make a visual determination as to whether or not all the ECG waveforms in the current display batch are substantially identical, from an interpretive point of view.

With the batch displayed, the cardiologist has several options available. The cardiologist can alter the placement of the caliper positions on any displayed ECG waveform. Also, the cardiologist can assign a new interpretation to all or any subset of the ECG waveforms currently displayed. For example, the cardiologist can input commands to the computer to change the interpretation from "normal waveform" to "atrial fibrillation waveform." Additionally, the cardiologist can accept and confirm the interpretation and the caliper positions of all or any subset of the ECG waveforms displayed. Also, the cardiologist can accept and confirm all of the ECG waveforms in the current group, which includes not only the ECG waveforms in the current display batch, but also the remainder of the ECG waveforms in the group that are not currently displayed. Moreover, the cardiologist can input a command to indicate that an ECG waveform has "artifacts," if the computer did not previously identify and flag the artifacts.

Once the cardiologist has made all the desired changes and accepted all the correct values, the computer checks to see what batches, groups, and ECG waveforms still need to be interpreted. If there are still unviewed ECG waveforms in the current display group, the computer selects a new batch for display. If the current display group has been completely reviewed, the computer selects a new group for display. The cardiologist can also instruct the computer to repeat the grouping process or to generate new preliminary interpretations.

In one implementation, the computer separately displays all of the ECG waveforms so that the cardiologist can examine and verify the placement of the caliper positions. As noted previously, verifying the caliper positions can be performed after determining that each ECG waveform in a SVG has an associated set of caliper positions for measuring certain aspects of the waveform, such as the QT interval. This verification operation generally would be done if the computer performed its automated preliminary interpretation process based on the caliper positions.

The ECG waveforms may be displayed in a tall scrolling list, with one ECO waveform per line. In such a case, the cardiologist may select the ECG or Holter lead waveforms to be displayed, and each selected ECG or Holter lead is overlaid into the same graph space, and visually differentiated by color. This process allows the cardiologist to choose the Holter lead or combination of Holter leads to use when verifying the caliper positions. Also, the computer may enable the cardiologist to adjust the caliper positions in situ. Moreover, the computer may enable the cardiologist to zoom in on or otherwise enlarge each ECG waveform, so that the calipers can be adjusted with greater precision, if necessary. After the cardiologist has reviewed and approved of the caliper settings and positions for an entire scrolling list, the cardiologist can input a command to accept the entire list.

As noted earlier, the computer receives feedback from the cardiologist and integrates this feedback into the preliminary interpretation algorithm. With respect to the changes in the caliper positions, the computer may uses the cardiologist's feedback to train or modify the operations or applications that the computer performs in earlier stages of the process. Specifically, the cardiologist provides the computer with valuable expert information regarding caliper positions, and the computer uses such information to improve the manner in which calipers are positioned in the future. In the case in which an automated system determines the caliper positions, the computer can generate electronic records that can be used to train the automatic system. In the case of human technicians, the computer can generate reports comparing the initial and corrected caliper placements, which can be used as part of the technician's ongoing training.

Once all the ECG waveforms for a single SVG have been processed, the computer repeats the process for another SVG.

In one illustrative, non-limiting embodiment, with respect to the display mechanism for the computer, there are two basic operating principles. First, the display mechanism shows multiple ECG waveforms on the screen at a single time, in such a way that the cardiologist can readily determine whether they are substantially similar to each other. Second, the display mechanism allows the cardiologist to rapidly select and process any desired subset of the ECG waveforms. This processing might entail accepting the existing interpretation, replacing the existing interpretation with a new interpretation, or other actions. The display mechanism also enables the cardiologist to examine the ECG waveforms rapidly for similarities or differences and to select any chosen subset of the ECG waveforms. Then, the computer processes the whole subset with a single operation. Also, displaying multiple waveforms allows the cardiologist to work more quickly if the ECG waveforms are similar, and grouping the ECG waveforms according to the grouping metric ensures that each displayed batch of ECG waveforms will generally be very similar.

To display multiple ECG waveforms in the most visually useful way, the computer generally aligns them in time. In one example, the computer displays each set of ECG waveforms in such a way that the various ECG waveform features (e.g., PRS complex, R peak, Q-T interval, etc.) are all closely or exactly aligned. Exact alignment will not always be possible, since the ECG waveforms will not always be identical, but as long as the ECG waveforms are aligned closely, the cardiologist will still be able to evaluate the waveforms quickly.

Figure 8:
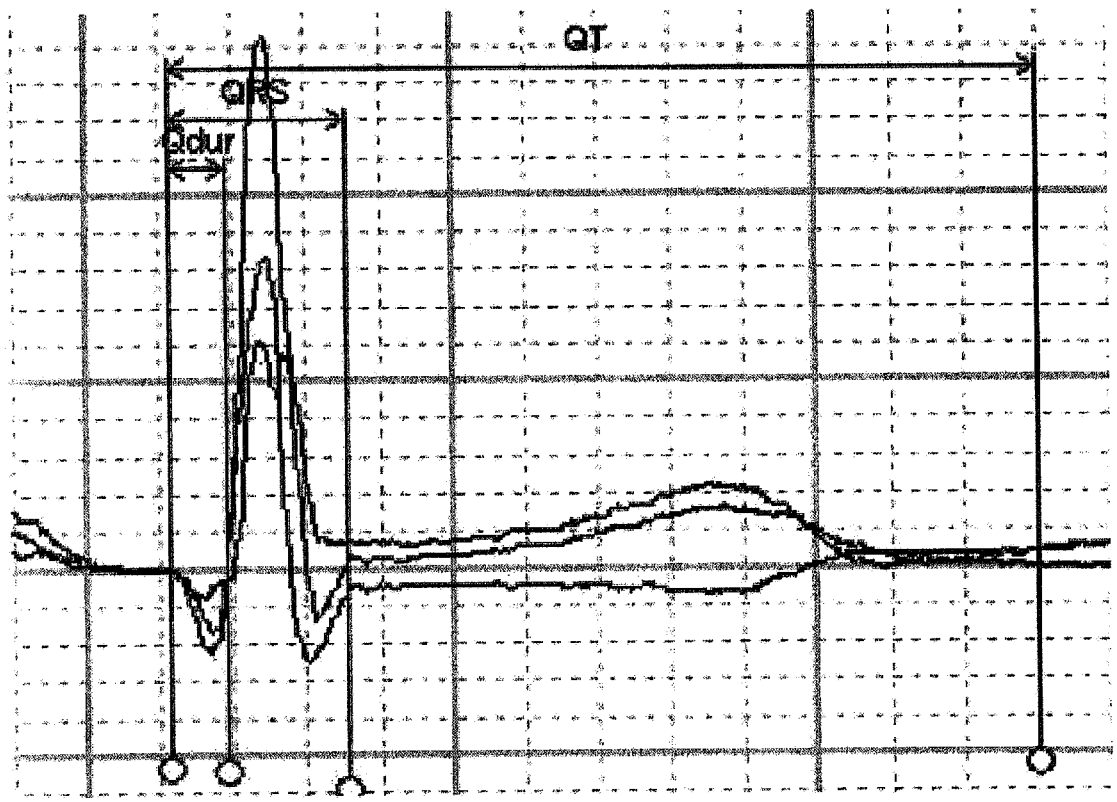
FIG. 8 is a non-limiting example of three waveforms that are aligned based on their respective R peaks.

One method of aligning ECG waveforms is to align the waveforms based on their R peaks. FIG. 8 shows an example in which three waveforms are aligned based on their R peaks. Automatic identification of the R peak of an ECG waveform is a reasonably well-known and standard technique. Once the R peak of each ECG waveform is identified, simply aligning the R peaks of each successive ECG waveform results in ECG waveforms that are acceptably well aligned.

Another method of aligning ECG waveforms is to align the waveforms based alignment based on an RMS error minima to smooth the waveforms. This method overlaps a pair of ECG waveforms at various time offsets, and calculates the RMS (root mean square) of the difference between the voltages at each point of the two ECG waveforms. This will yield a curve with a minimum value at the time offset that gives a very good alignment between the ECG waveforms.

Figure 9:
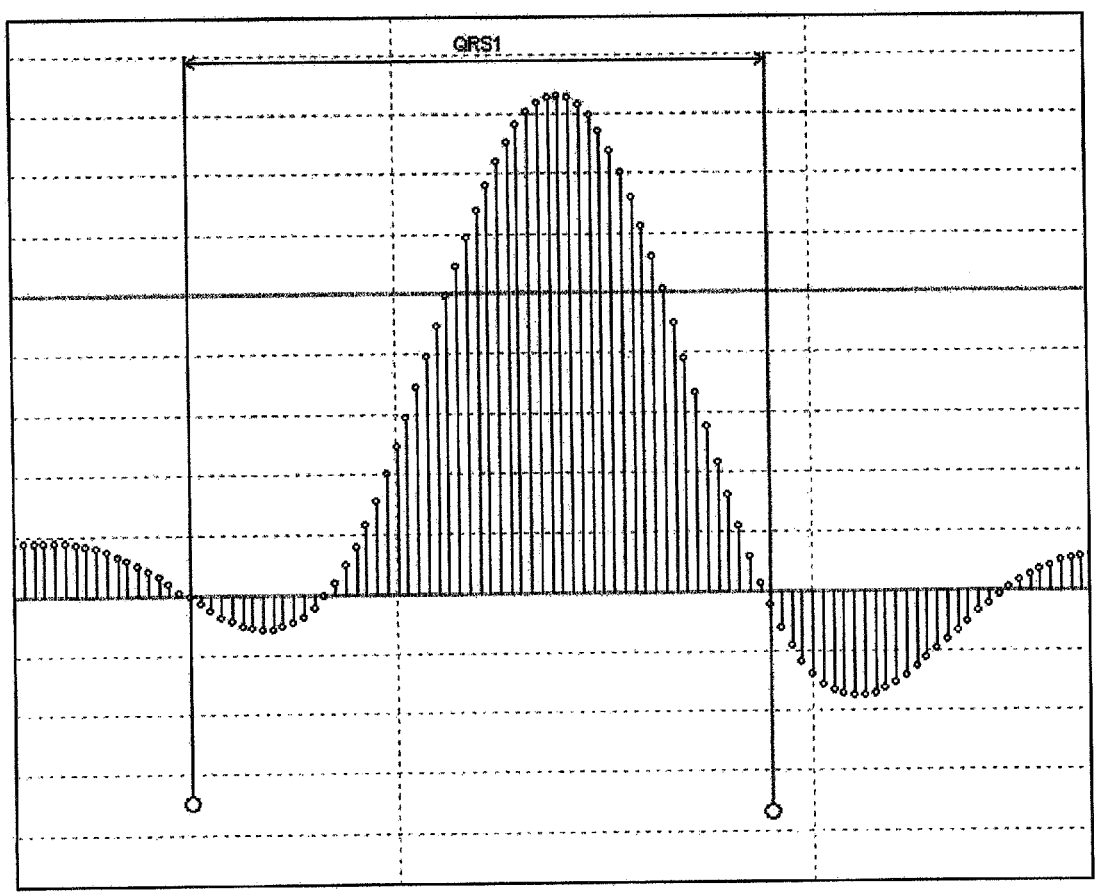
FIG. 9 is a non-limiting example of a waveform showing the area under the curve (AUC) that a computer may analyze to align waveforms.

Another method of aligning ECG waveforms is to align them based on an "area under curve" ("AUC") maxima. This method compares areas under corresponding portions of two ECG waveforms to find an optimum time alignment. For example, as shown in FIG. 9, the computer may evaluate the area under the QRS complex (FIG. 1), which is labeled as QRS1 in FIG. 9. When the ECG waveforms are lined up well, their common AUC will be at a peak.

Figure 6:
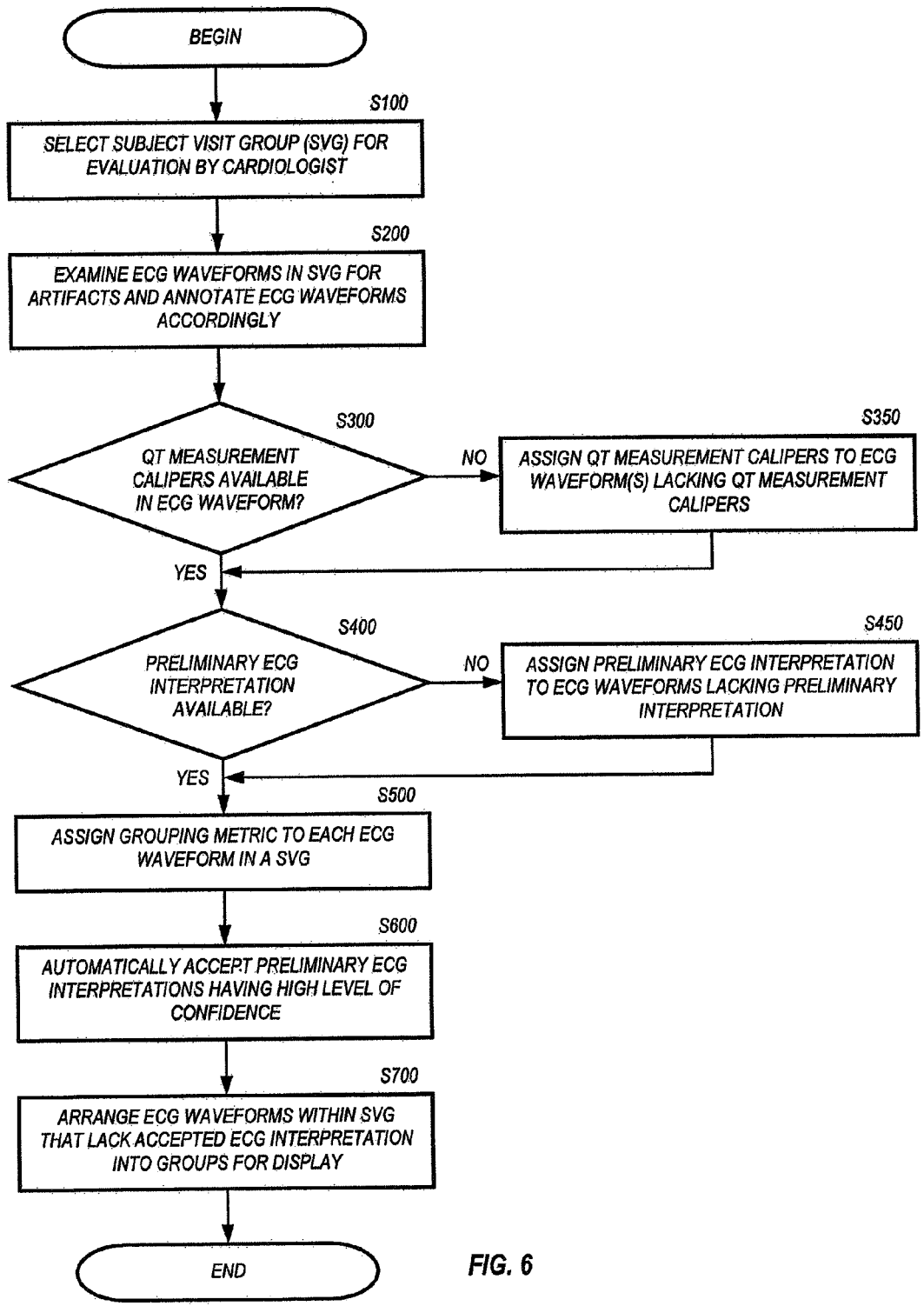
FIG. 6 is a flowchart illustrating a non-limiting example of a method of rapidly interpreting electrocardiograph tracings.

FIG. 6 shows a flowchart illustrating a non-limiting example of a process that the computer executes to rapidly interpret ECG tracings.

First, the computer selects an SVG for evaluation (S100). As discussed earlier, the computer may select the SVG that has not been processed and that has been stored for the longest period of time. Alternatively, the computer may choose the SVG based on the results of a preliminary interpretation or based on the results of a preliminary (but non-interpretive) screening. The preliminary interpretation or screening may be done by a human technician or by an automatic computerized process. Of course, the cardiologist can instruct the computer to select any particular SVG to interpret.

Then, the computer examines each ECG waveform in the SVG to determine if any of the waveforms contain "artifact" (S200). If an ECG waveform contains artifact, the computer marks the ECG waveform with an appropriate designation. For example, the computer may add an annotation to an overlay (e.g., the RR interval (FIG. 1)) in the ECG waveform. While the computer may automatically detect the artifact using an appropriate software analysis program, the cardiologist can "manually" annotate the ECG waveform, for example, as "Unmeasurable, Uninterpretable," by inputting appropriate commands to the computer.

After the ECG waveforms are annotated, each ECG waveform in the SVG is analyzed to determine whether or not it contains caliper positions for measuring various aspects of the waveform, such as the QT interval. (S300). The caliper positions will normally be part of the imported data, and they may be generated by an ECG recorder, a human technician, a computer process other than the ECG recorder, or other means. Also, the computer may automatically analyze each ECG waveform to determine if it contains caliper positions. Alternatively, the cardiologist may manually inspect each waveform and input a command indicating whether or not the waveform has caliper positions.

If any ECG waveform lacks caliper positions (S300: No), then the computer analyzes the ECG waveform and, if possible, assigns caliper positions to the waveform. Alternatively, the cardiologist can review the ECG waveforms and assign caliper positions by inputting appropriate commands to the computer.

Subsequently, the computer determines whether or not a preliminary interpretation is available for each ECG waveform (S400). Typically, a preliminary interpretation might be embedded within the ECG waveform data and may be created by a human technician or by another computer program. If no preliminary interpretation exists for any of the ECG waveforms (S400: No), the computer generates preliminary interpretations for the waveforms. Also, in one implementation, if the computer performs a preliminary interpretation for any of the ECG waveforms, it performs the interpretations for all of ECG waveforms in the SVG.

Afterwards, the computer examines each ECG waveform and assigns a group metric to each waveform (S500). As noted above, the group metric may be a set values that reflects certain key aspects of each ECG waveform and can be used to determine how similar two ECG waveforms are to each other.

In addition, the computer may determine whether or not any of the ECG waveforms in the SVG have a preliminary interpretation that is so reliable that it can be accepted without cardiologist approval (S600). If an ECG waveform has a preliminary interpretation that is sufficiently reliable, the computer exempts the waveform from further analysis, and exempting reliably interpreted waveforms reduces the cardiologist's workload.

Next, the computer analyzes the grouping metrics, as well as other available information, of the ECG waveforms in the SVG and groups similar ECG waveforms within the SVG with each other (S700). During the grouping analysis, the computer considers the presence of any artifacts, as detected previously or as indicated by the cardiologist. Also, the computer may consider the presence of any existing preliminary interpretation, cardiologist-provided interpretation, or automatically-accepted interpretation. Furthermore, if verified caliper positions are available, the computer may take them into account in the grouping analysis, along with the other grouping metrics.

Figure 7A:
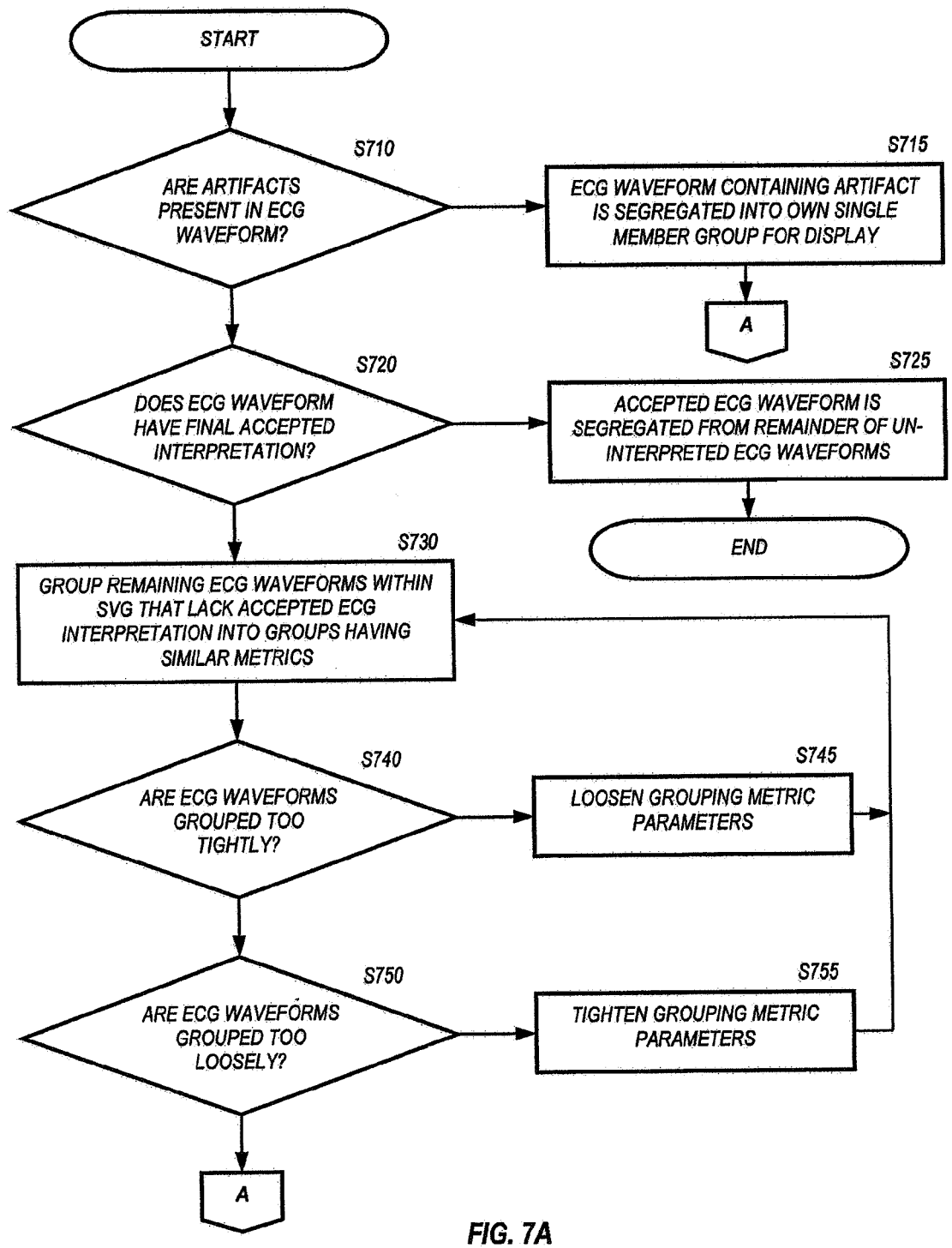
FIG. 7A is a flowchart illustrating a first portion of a non-limiting example of a method of grouping of electrocardiograph tracings based on metrics for cardiologist interpretation.
Figure 7B:
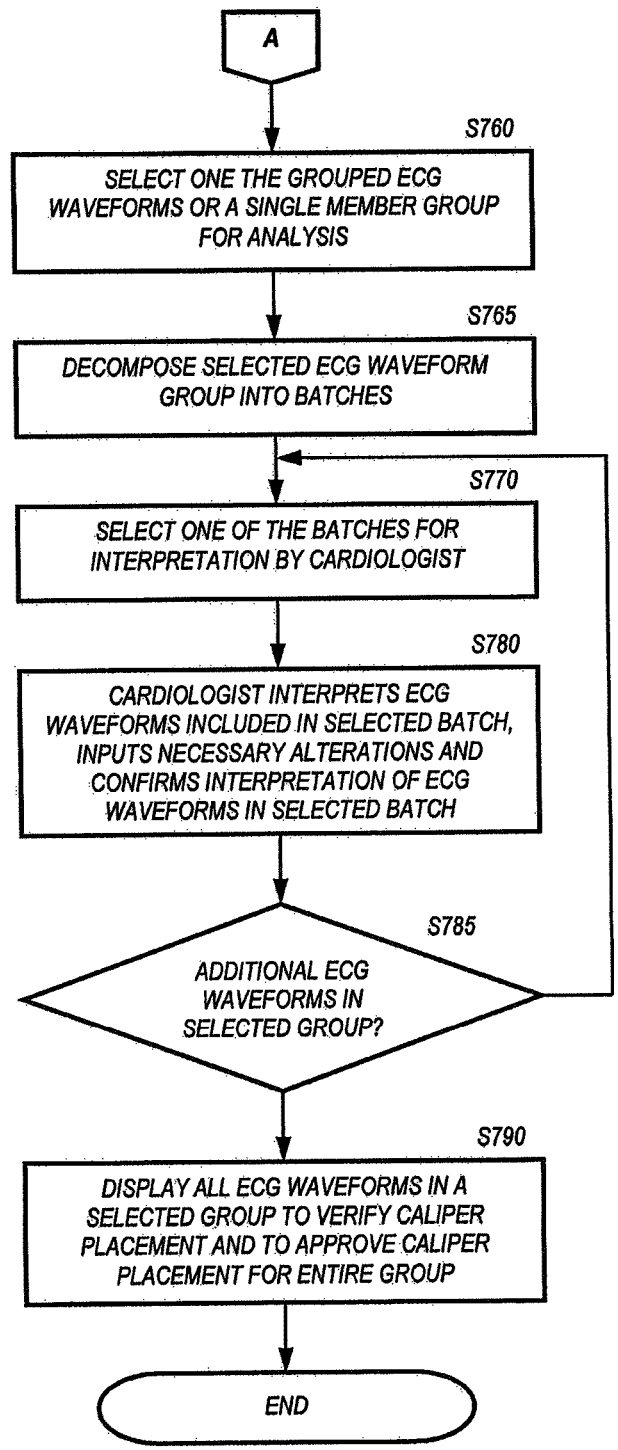
FIG. 7B is a flowchart illustrating a second portion of a non-limiting example of grouping of electrocardiograph tracings based on metrics for cardiologist interpretation.

FIGS. 7A and 7B show a flowchart illustrating a non-limiting example of a process that the computer executes to group similar ECG waveforms within the SVG with each other.

Initially, the computer determines if any of the ECG waveforms within the SVG contain artifacts (S710). If an artifact is present in an ECG waveform (S710: Yes), the computer assigns the waveform to its own single-member group (S715).

Similarly, the computer determines if any of the ECG waveforms in the SVG has a final, accepted interpretation (S720). In one embodiment, the computer determines that the waveform has a final, accepted interpretation if the computer determined that it had a sufficiently reliable preliminary interpretation in operation S600. Alternatively or additionally, the computer may determine that a waveform has a final, accepted interpretation if the cardiologist has previously designated the waveform as being finally accepted. If an ECG waveform has a final, accepted interpretation (S720: Yes), the computer does not include it in any group at all, regardless of whether the final, accepted interpretation came from the cardiologist or an automatic computer process (S725).

Next, the computer groups the remaining ECG waveforms, which do not contain artifacts and which do not have final, accepted interpretations, according to their group metric values (S730). In other words, the computer places the remaining ECG waveforms into one or more groups, according to their similarity, such that each group only contains waveforms that are substantially similar to each other.

As noted above, the cardiologist has the ability to control the coarseness or fineness of the grouping of ECG waveforms. For example, when the computer groups the ECG waveforms, it possibly may group them too tightly (e.g., ECG waveforms that should be in different groups are lumped together) or too loosely (e.g., ECG waveforms that should be combined are grouped apart). Either situation creates more work for the cardiologist. Therefore, the cardiologist has the ability to instruct the computer to tighten or loosen the manner in which it groups the waveforms.

Specifically, if the cardiologist believes that the ECG waveforms are grouped too tightly (S740: Yes), he or she can instruct the computer to loosen the parameters of the group metrics that the computer uses to group ECG waveforms (S745). Conversely, if the cardiologist believes that the ECG waveforms are grouped too loosely (S750: Yes), he or she can instruct the computer to tighten the parameters of the group metrics that the computer uses to group ECG waveforms (S755). Also, as described previously, the computer may employ an SOM to indicate the relationship between the various groups. Specifically, similar ECG waveforms are placed in respective groups, and the SOM identifies similarities among the groups.

After the computer has initially grouped the ECG waveforms in a particular SVG, the computer may display the waveform groups on a display so that the cardiologist can evaluate the groups. The display could contain a screen having a number of boxes, and each box could show all the ECG waveforms that are assigned to a single group. Also, the computer may overlay the ECG waveforms, and the doctor can select the Holter lead by using a mouse or other device to move a cursor to the lead and select it. If there are too many boxes to fit on the screen at one time, a scrolling display may be created, and the computer may prioritize the groups based on the number of waveforms that they contain. Then, the computer could display the boxes corresponding to the most populous groups at the top of the scrolling display.

As noted in FIG. 7B, the computer selects which group of ECG waveforms to display for analysis (S760). For example, as described above, the computer may automatically display the largest groups first or may display the smallest groups first. In another implementation, the computer uses the pre-existing interpretive statements, in combination with a grading system, to determine which group to display. Also, the cardiologist may be able to input a command to select which group he or she would like the computer to display.

Once a group of ECG waveforms is selected for display, the computer decomposes the waveforms into one or more batches (S765). For example, the display may not be able to display the entire group of ECG waveforms at once because there may be a limit (based upon the computer hardware and/or software) on how many ECG waveforms can be simultaneously displayed. If not all the ECG waveforms can be displayed, the group of waveforms is divided into batches such that the number of waveforms in each batch is less than or equal to the maximum number of waveforms that the computer can display at once. Also, the batch may contain an entire group of ECG waveforms, if the entire group of waveforms does not exceed the limitations of the computer display.

Then, one of the batches of waveforms of the current group is selected to be presented to the cardiologist (S770). Accordingly, the cardiologist evaluates the ECG waveforms in the displayed batch and determines whether or not they are substantially the same (S780).

For example, while the batch displayed, the cardiologist can alter the placement of the caliper positions on any displayed ECG waveform. Also, the cardiologist can assign a new interpretation to all or any subset of the ECG waveforms currently displayed. Additionally, the cardiologist can accept and confirm the interpretation and the caliper positions of all or any subset of the ECG waveforms displayed. Also, the cardiologist input a command to indicate that an ECG waveform has "artifacts," if the computer did not previously identify and flag the artifacts.

Once the cardiologist has made all the desired changes and accepted all the correct values, the computer checks to see what batches, groups, and ECG waveforms in the SVG still need to be interpreted (S785). If there are still unviewed ECG waveforms in the current display group, the computer selects a new batch for display. (S785: Yes).

If the current display group has been completely reviewed (S785: No), the computer displays all of the ECG waveforms in the group so that the cardiologist can examine, verify, and approve of the placement of the caliper positions for the group (S790). Also, as noted above, the ECG waveforms may be displayed in a tall scrolling list, with one ECG waveform per line. In such a case, the cardiologist may select the ECG or Holter lead waveforms to be displayed, and each selected ECG or Holter lead is overlaid into the same graph space, and visually differentiated by color. This process allows the cardiologist to choose the ECG or Holter lead or combination of ECG or Holter leads to use when verifying the caliper positions. Also, the computer may enable the cardiologist to adjust the caliper positions, as discussed above.

As previously noted, the computer receives feedback from the cardiologist and integrates this feedback into the preliminary interpretation algorithm. With respect to the changes in the caliper positions, the computer may use the cardiologist's feedback to train or modify the operations or applications that the computer performs in earlier stages of the process. Specifically, the cardiologist provides the computer with valuable expert information regarding caliper positions, and the computer uses such information to improve the manner in which calipers are positioned in the future. In the case in which an automated system determines the caliper positions, the computer can generate electronic records that can be used to train the automatic system. In the case of human technicians, the computer can generate reports comparing the initial and corrected caliper placements, which can be used as part of the technician's ongoing training.

Also, the manner in which the ECG waveforms are finally interpreted and grouped are fed back to the computer, and the computer uses such information to assist it with its interpretation and grouping of future waveforms.

Once all the ECG waveforms for a single SVG have been processed, the computer repeats the process for another SVG.

The foregoing description of the exemplary embodiments of the invention has been presented for purposes of illustration and description. It is not intended to be exhaustive or to limit the invention to the precise form disclosed, and modifications and variations are possible in light of the above teachings or may be acquired from practice of the invention. The exemplary embodiments were chosen and described in order to explain the principles of the invention and its practical application to enable one skilled in the art to utilize the invention in various exemplary embodiments and with various modifications as are suited to the particular use contemplated.

Thus, while only certain exemplary embodiments of the invention have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the exemplary embodiments described therein.

The invention claimed is:
1. A method for analyzing a subject-visit group of ECG waveforms, the method comprising:

selecting a subject-visit group for a particular patient from a plurality of subject-visit groups;

analyzing each ECG waveform of the subject-visit group to determine whether artifacts are present and annotating each ECG waveform containing artifacts;

determining if measurement calipers are present in each ECG waveform and adding measurement calipers to each ECG waveform lacking measurement calipers;

assigning a grouping metric to each ECG waveform; and segregating the ECG waveforms according to their grouping metric for display and evaluation.

2. The method according to claim 1, wherein the method further comprises assigning a preliminary interpretation to each ECG waveform that lacks a preliminary interpretation.

3. The method according to claim 2, wherein the method further comprises automatically accepting preliminary interpretations of each ECG waveform having a predetermined level of confidence.

4. The method according to claim 1, wherein the segregating the ECG waveforms comprises segregating ECG waveforms having an accepted interpretation from other ECG waveforms being grouped for interpretation.

5. The method according to claim 1, wherein the segregating the ECG waveforms further comprises segregating the ECG waveforms containing artifacts into a single member group for interpretation.

6. The method according to claim 5, wherein the segregating the ECG waveforms further comprises grouping ECG waveforms lacking an accepted interpretation into groups based on a set of predetermined metrics.

7. The method according to claim 6, wherein the predetermined metrics are adjusted to control the grouping of the ECG waveforms lacking an accepted interpretation.

8. The method according to claim 1, wherein the method further comprises:

selecting a group of segregated ECG waveforms for interpretation;

interpreting sub-groups of the group of segregated ECG waveforms; and confirming the caliper placement for the group of segregated ECG waveforms.

9. A method for analyzing a subject-visit group of ECG waveforms, the method comprising:

selecting a subject-visit group for a particular patient from a plurality of subject-visit groups;

analyzing each ECG waveform of the subject-visit group to determine whether artifacts are present and annotating each ECG waveform containing artifacts;

determining if measurement calipers are present in each ECG waveform and adding measurement calipers to each ECG waveform lacking measurement calipers;

assigning a grouping metric to each ECG waveform;

segregating the ECG waveforms according to their grouping metric for display and evaluation; and interpreting a group of segregated ECG waveforms by:

determining if placement of QT measurement calipers on an ECG waveform is necessary; and assigning an interpretation to an ECG waveform of the group of segregated ECG waveforms.

10. The method according to claim 9, wherein the method further comprises accepting the QT measurement placement and interpretation of at least one ECG waveform of the group of segregated ECG waveforms.

* * * * *